United States Patent [19]

Dumić et al.

[11] Patent Number: 5,635,529
[45] Date of Patent: Jun. 3, 1997

[54] SULFONAMIDODIOXEPANES, METHODS OF PREPARATION, INTERMEDIATES, SALTS AND USE THEREOF

[75] Inventors: Miljenko Dumić; Darko Filič, both of Zagreb; Mladen Vinković, Čakovec; Blanka Jamnicky, Zagreb, all of Croatia

[73] Assignee: PLIVA farmaceutska, kemijska, prehrambena i kozmeticka industrija, dionicko drustvo Zagreb, Zagreb, Croatia

[21] Appl. No.: 390,358

[22] Filed: Feb. 17, 1995

[30] Foreign Application Priority Data

Feb. 21, 1994 [HR] Croatia ................................ P940124A

[51] Int. Cl.$^6$ .......................... A01N 43/32; C07D 321/00
[52] U.S. Cl. .......................... 514/452; 514/884; 549/333; 549/347
[58] Field of Search .................... 549/347, 333; 548/218; 514/452, 884

[56] References Cited

PUBLICATIONS

Chemical Abstract vol. 83 No. 164098 (1975) "Stereocontrolled route to a key intermediate for the synthesis of maytansine".

Primary Examiner—C. Warren Ivy
Assistant Examiner—Raymond Covington
Attorney, Agent, or Firm—Law Offices of Pollock, Vande Sande & Priddy

[57] ABSTRACT

Novel O-substituted or O-unsubstituted 6-sulfonamido-1,3-dioxepane-5-ols having hypoglycemic activity are obtained from 6-amino-1,3-dioxepane-5-ol, tetrahydro-6H-[1,3]-dioxepino[5,6-d]oxazole, 5,6-epoxy-1,3-dioxepane or N-sulfonyl-tetrahydro-1H,4H-[1,3]-dioxepino[5,6-b]azirine as starting materials.

20 Claims, No Drawings

SULFONAMIDODIOXEPANES, METHODS OF PREPARATION, INTERMEDIATES, SALTS AND USE THEREOF

FIELD OF THE INVENTION

The invention relates to novel sulfonamidodioxepanes, methods and intermediates for their preparation, the salts thereof, pharmaceutical preparations containing novel compounds and the use thereof.

SUMMARY OF THE INVENTION

Compounds of general formula I

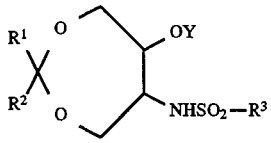

wherein $R^1$ and $R^2$ represent a hydrogen atom, a straight-chain or branched alkyl with 1–4 C atoms or phenyl, or $R^1 + R^2$ together represent an alkylidene group with 4–6 C atoms, $R^3$ represents a straight-chain or branched alkyl with 1–4 C atoms, a straight-chain or branched mono- to perfluoroalkyl with 1–4 C atoms, and an o-, m- or p-substituted phenyl group

wherein

X represents a hydrogen atom, a lower straight-chain or branched alkyl with 1–4 C atoms, a trifluoromethyl group, a halogen atom with atomic number 9-53, a hydroxy, alkoxy, amino, alkyl- or dialkylamino, acylamino or hydroxyamino group, and Y represents a hydrogen atom, a lower straight-chain or branched alkyl with 1–4 C atoms, a benzyl or sulfonyl group

wherein $R^3$ has the above described meanings or represents an acyl group

wherein $R^4$ represents a lower straight-chain or branched alkyl with 1–4 C atoms or a benzyl group, and their physiologically acceptable salts.

DETAILED DESCRIPTION OF VARIOUS AND PREFERRED EMBODIMENT(S)

Compounds such as those shown above have not been previously known. Now it has been found that these compounds have valuable pharmacological properties, especially hypoglycemic activity, irrespective of their application route that can be intravenous, subcutaneous or oral. Hypoglycemic activity has been determined by standard tests on warm-blooded animals, for example mice.

In the compounds of the general formula I, alkyl and alkoxy represent methyl, ethyl, propyl, isopropyl, butyl, isobutyl, sec.-butyl and tert.-butyl, and methoxy, ethoxy, propoxy, isopropoxy, butoxy, sec.-butoxy, tert.-butoxy and isobutoxy groups. Acyl group is derived from aliphatic, arylaliphatic or aromatic carboxylic acids, for example formic acid, acetic acid, propionic acid, butyric acid, phenylacetic acid or benzoic acid.

With bases, the novel compounds of the general formula I form salts. The salts are also a subject of the present invention. Examples of such salts are alkali and alkaline-earth salts, such as sodium, potassium, magnesium or calcium salts.

Novel compounds of the general formula I can be prepared according to the first process of the invention by condensing compounds of the general formula II

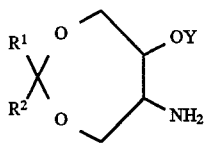

wherein $R^1$, $R^2$ and Y have the above described meanings, with reactive derivatives of sulfonic acids of the general formula III $$R^3SO_2-Z \quad \text{III}$$

wherein $R^3$ has the above described meanings and

Z represents a halogen atom with atomic number 9 to 17 or $-OSO_2R^3$ group, wherein $R^3$ has the above described meanings. The reaction may be carried out in water-miscible or water-unmiscible inert organic solvents, in the presence or absence of water, in the presence or absence of inorganic or organic acid-binding agents, at temperatures from −50° C. to +50° C., preferably at −10° C. to +10° C., and, optionally, converting the obtained compounds with inorganic bases or metal alcoholates into pharmaceutically acceptable salts.

Suitable inert solvents are, for example, hydrocarbons such as toluene or xylene; lower alcohols with up to 6 C atoms, such as methanol or ethanol; ethers such as diethylether, dioxane or tetrahydrofuran; chlorinated hydrocarbons, such as methylene chloride or chloroform; lower ketones with up to 6 C atoms, such as acetone, methyl ethyl ketone or methyl isobutyl ketone; carboxylic acid esters, such as ethyl acetate; carboxylic acid nitriles, such as acetonitrile; amides, such as dimethyl formamide or HMPT; sulfoxides; such as dimethyl sulfoxide; or sulfones, such as sulfolane.

As suitable inorganic bases, alkali and alkaline-earth hydroxides, hydrogen carbonates, carbonates or phosphates, that is sodium or potassium and magnesium or calcium compounds can be used.

Suitable organic bases are tertiary amines, such as triethylamine, dimethylaniline, pyridine, DBN or DBU.

Suitable starting materials of the general formula II are compounds that are appropriately substituted in accordance with the definition of symbols $R^1$, $R^2$ and Y as given at formula I. One such group of starting materials is 6-amino-1,3-dioxepane-5-ols, which can easily be prepared, for example, by hydrolysis of appropriate 6-acetylamino-5-chloro-1,3-dioxepanes (M. Sovak and R. Ranganathan, U.S. Pat. No. 4,389,526) and amonolysis of epoxy-1,3-dioxepanes (M. Sovak and R. Ranganathan, EP 33 426; A. V. Rama Rao et al., Indian J. Chem. 22B (1983) 419).

According to the second process of the invention, the novel compounds of the general formula I can be prepared by reacting oxazolines of the general formula IV

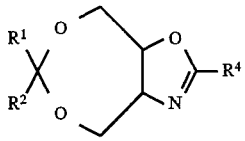

wherein $R^1$, $R^2$ and $R^4$ have the above described meanings, with reactive derivatives of sulfonic acids of general formula III, wherein $R^3$ and Z have the above described meanings. The reaction is carried out in non-aqueous inert organic solvents, in the presence of inorganic or organic acid-binding agents. Optionally the obtained derivatives of the general formula I ($Y=\!\!-\!\!COR^4$) may be hydrolyzed or alcoholized into derivatives of formula I ($Y=H$). Optionally the obtained compounds may be converted with inorganic bases and metal alcoholates into pharmaceutically acceptable salts. The method of performing this process is identical to the method of the first process, with the exception that it has to be performed in a non-aqueous medium.

Suitable starting materials of the general formula IV are compounds that are appropriately substituted in accordance with the definition of symbols $R^1$, $R^2$ and $R^4$ as given at formula I. They can be easily prepared by dehydrohalogenation cyclisation of the corresponding 6-acylamino-5-chloro-1,3-dioxepanes (M. Dumić et al., Org. Prep. Proced. Int. 24, (1992) 536 and ibid. 25, (1992) 373).

According to the third process of the invention, novel compounds of the general formula I can be prepared by reacting epoxides of general formula V

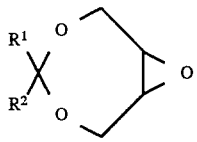

wherein $R^1$ and $R^2$ have the above described meanings, with sulfonamides of general formula VI

          VI wherein $R^3$ has the above described meanings, by means of heating both reactants in the absence or in the presence of inert organic solvents such as, for example, aromates, such as toluene or xylene, chlorinated hydrocarbons, such as methylene chloride chloroform or dichlorethane, carboxylic acid esters, such as ethyl acetate; ethers, such as diisopropylether or dioxane; amides, such as dimethyl formamide, dimethyl acetamide or HMPT; surfoxides, such as dimethylsulfoxide; or sulfones, such as sulfolane, at temperatures from 25° C. to 300° C. and preferably between 100° C. and 200° C. Optionally, the obtained compounds may be converted with inorganic bases or metal alcoholates into pharmaceutically acceptable salts.

Suitable starting materials of the general formula V are compounds that are appropriately substituted in accordance with the definition of symbols $R^1$ and $R^2$ at formula I. They can be easily prepared by epoxydation of suitable dihydrodioxepines (J. Soulier et al., C. R. Acad. Sci. Ser. C. 280, (1975) 681; W. J. Elliot et al., J. Org. Chem. 41, (1976) 2469; A. J. Biloski, Synthesis 1980, 810).

According to the fourth process of the invention, novel compounds of the general formula I can be prepared by hydrolyzing N-sulfonyl-dioxepinoazirines of the general formula VII

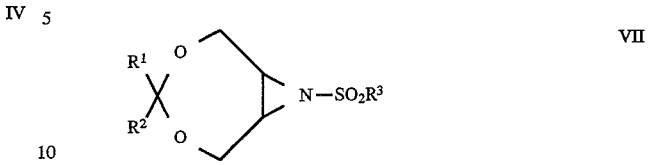

wherein $R^1$, $R^2$ and $R^3$ have the above described meanings, in water or in water-miscible organic solvents, in the presence of inorganic bases, at temperatures from 0° C. to 150° C., preferably at 50° C. to 100° C. Optionally, the obtained compounds may be converted with inorganic bases or metal alcoholates into pharmaceutically acceptable salts.

As organic solvents there can be used alcohols with up to 6 C atoms, such as methanol, ethanol or tert.-butanol; ethers, such as dioxane or tetrahydrofurane; chlorinated hydrocarbons, such as methylene chloride or chloroform; ketones such as acetone; amides, such as dimethylformamide or HMPT; amines such as pyridine; sulfoxides, such as dimethylsulfoxid; or sulfones, such as sulfolane. As bases, alkali metal hydroxides or carbonates, that is, lithium, sodium or potassium compounds, can be used.

Suitable starting materials of the general formula VII are compounds that are appropriately substituted in accordance with the definition of symbols $R^1$, $R^2$ and $R^3$ at formula I. They can be prepared by sulfonation of convenient dioxepinoazirines (M. Dumić et al., WO 93 04,067; Tetrahedron Lett. 34 (1993) 3639).

Optionally, novel compounds of the general formula I obtained according to the processes (1–4) of the invention, may be converted into their pharmaceutically acceptable salts by reacting the compounds of the general formula I with an equimolar amount of an inorganic base, alkali hydroxide, for example, sodium hydroxide, or alkali alcoholate, such as sodium methylate, in inert organic solvents, such as methanol, ethanol, acetone, toluene, diisopropylether.

Novel compounds of the general formula I prepared according to the processes of the invention or their pharmaceutically acceptable salts show a significantly to strongly expressed hypoglycemic activity in a model of diabetes in mice induced by streptozotocine, irrespective of the administration route. The administration route can be intravenous, subcutaneous or oral. For example, 4 hours after subcutaneous application of cis-6-sulfanylamido-1,3-dioxepane-5-ol in a dose of 20 mg/kg to mice with diabetes induced by streptozocine, a concentration of glucose in blood was reduced for 16.6%. That is, the level of glucose was 83.4% of the level present in untreated hyperglycemic animals.

In view of the above, novel sulfonamidodioxepanes of the general formula I and their pharmaceutically acceptable salts represent effective hypoglycemic agents. By conventional processes of pharmaceutic technology, they can be converted into suitable pharmaceutical formulations such as tablets, pills, powders, capsules, granules, solutions, etc. of short-term or prolonged activity for therapy of diabetes mellitus.

The present invention is illustrated, yet in no way limited, by the following examples.

EXAMPLE 1

A mixture of trans-6-amino-1,3-dioxepane-5-ol (0.30 g), 4-acetyl-aminobenzenesulfochloride (0.58 g), pyridine (0.40 ml) and methylene chloride (10.0 ml) was stirred at the temperature of 0° C. for 60 minutes. After evaporation of the solvent at reduced pressure, the evaporation residue was chromatographed on a silica gel column by elution with ethyl acetate.

Trans-6-(4-acetylaminobenzenesulfonamido)-1,3-dioxepane-5-ol was obtained. M.p. 210°–211° C./ethyl acetate-methanol (9.5:0.5)

EXAMPLE 2

A mixture of cis-2-methyl-3a,4,8,8a-tetrahydro-6H-[1,3]-dioxepino-[5,6-d]oxazole (1.00 g), 4-acetylaminobenzenesulfochloride (1.50 g), pyridine (1.05 ml) and methylene chloride (60.0 ml) was stirred at room temperature for 90 minutes. After addition of water (10.0 ml), the mixture was stirred for further 15 minutes at the same temperature. The product was extracted with methylene chloride, the extract was dried over anhydrous sodium sulfate, methylene chloride was evaporated at reduced pressure and the evaporation residue was chromatographed on a silica gel column by elution with a mixture of ethyl acetate/methanol (9.8:0.2).

Cis-6-(4-acetylaminobenzenesulfonamido)-5-acetoxy-1,3-dioxepane was obtained. M.p. 184°–186° C./ethyl acetate-methanol (6:1).

A mixture of cis-6-(4-acetylaminobenzenesulfonamido)-1,3-dioxepane (0.150 g), 25% ammonia (3.0 ml) and 96% ethanol (6.0 ml) was stirred at room temperature for 3 hours. The mixture was then evaporated to dryness at reduced pressure and by the recrystallization of the evaporation residue from ethyl acetate/methanol (1:1) mixture, cis-6-(4-acetylaminobenzenesulfonamido)-1,3-dioxepane-5-ol was obtained, m.p. 161°–163° C.

EXAMPLE 3

A mixture of 5,6-epoxy-1,3-dioxepane (0.5 g) and of 4-acetylaminobenzenesulfonamide (0.92 g) was heated in a sealed ampule at the temperature of 150° C. for 15 minutes. The mixture was cooled to room temperature, chromatographed on a silica gel column by elution with a mixture of ethyl acetate-methanol (9.5:0.5) and trans-6-(4-acetylaminobenzenesulfonamido)-1,3-dioxepane-5-ol was obtained. M.p. 208°–210° C./ethyl acetate-methanol (6:1).

EXAMPLE 4

A mixture of 1-(4-acetylaminobenzenesulfonyl)-4,4-dimethyl-1a,2,6,6a-tetrahydro-1H,4H-[1,3]-dioxepino[5,6-b]azirine (0.33 g), potassium hydroxide (0.14 g) and water (2.6 ml) was boiled with reflux for 60 minutes. The mixture was cooled to room temperature, acidified with diluted hydrochloric acid to pH 6.5 and evaporated to dryness at reduced pressure. The chromatography of the evaporation residue on a silica gel column by elution with a mixture of ethyl acetate/methanol (9.8:0.2) yielded trans-6-(4-acetylaminobenzene-sulfonamido)-2,2-dimethyl-1,3-dioxepane-5-ol, m.p. 203°–205° C./methylene chloride-methanol (9:1), and trans-6-sulfanylamido-2,2-dimethyl-1,3-dioxepane-5-ol.

EXAMPLE 5

A mixture of 1-(4-acetylaminobenzenesulfonyl)-1a,2,6,6a-tetrahydro-1H,4H-[1,3{-dioxepino-[5,6-b]azirine (0.30 g), potassium hydroxide (0.10 g) and water (2.5 ml) was boiled with reflux for 60 minutes. The mixture was cooled to room temperature, acidified with diluted hydrochloric acid to pH 6.5 and evaporated to dryness at reduced pressure. The evaporation residue was chromatographed on a silica gel column by elution with a mixture of methylene chloride-methanol (10:1).

Trans-6-(4-acetylaminobenzenesulfonamido)-1,3-dioxepane-5-ol, m.p. 209°–211° C./ethyl acetate-methanol (1:1), and trans-6-sulfanylamido-1,3-dioxepane-5-ol, m.p. 162°–164° C./ethyl acetate-methanol (1:1), were obtained.

EXAMPLE 6

To a mixture of cis-6-amino-1,3-dioxepane-5-ol (0.30 g) and pyridine (0.40 ml) in methylene chloride (10.0 ml), a solution of 4-acetylaminobenzenesulfochloride (0.58 g) in methylene chloride (35.0 ml) was added, drop, by drop within 90 minutes at the temperature of 0° C. Subsequently, the mixture was stirred at the same temperature for further 15 minutes and then evaporated to dryness at reduced pressure. Chromatography of the evaporation residue on a silica gel column by elution with a mixture of methylene chloride-methanol (8:2) yielded cis-6-(4-acetylaminobenzenesulfonamido)-1,3-dioxepane-5-ol, m.p. 159°–161° C./ethyl acetate-methanol (2:1).

We claim:

1. Compounds of general formula I

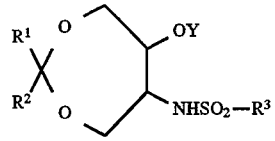

wherein $R^1$ and $R^2$ represent a hydrogen atom, a straight-chain or branched alkyl with 1–4 C atoms or phenyl, or $R^1+R^2$ together represent alkylidene group with 4–6 C atoms, $R^3$ represents a straight-chain or branched alkyl with 1–4 C atoms, a straight-chain or branched mono- to perfluoroalkyl with 1–4 C atoms, and an o-, m- or p-substituted phenyl group,

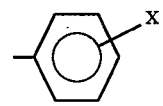

wherein

X represents a hydrogen atom, a lower straight-chain or branched alkyl with 1–4 C atoms, trifluoromethyl group, a halogen atom with atomic number 9–53, hydroxy, alkoxy, amino, alkyl- or dialkylamino, acylamino or hydroxyamino group, and Y represents a hydrogen atom, a lower straight-chain or branched alkyl with 1–4 C atoms, benzyl or sulfonyl group

wherein $R^3$ has the above described meanings or represents an acyl group

wherein $R^4$ represents a lower straight-chain or branched alkyl with 1–4 C atoms, or benzyl group, and their physiologically acceptable salts.

2. Compound according to claim 1, characterized in that $R^1=R^2=H$, cis, Y=H, $R^3=4—CH_3CONH—C_6H_4—$, and its pharmaceutically acceptable salts.

3. Compound according to claim 1, characterized in that $R^1=R^2=H$, trans, Y=H, $R^3=4—CH_3CONH—C_6H_4—$, and its pharmaceutically acceptable salts.

4. Compound according to claim 1, characterized in that $R^1=R^2=H$, cis, Y=H, $R^3=4—H_2N—C_6H_4—$, and its pharmaceutically acceptable salts.

5. Compound according to claim 1, characterized in that $R^1=R^2=H$, trans, Y=H, $R^3=4—H_2N—C_6H_4—$, and its pharmaceutically acceptable salts.

6. Compound according to claim 1, characterized in that $R^1=R^2=H$, cis, Y=H, $R^3=C_6H_5—$, and its pharmaceutically acceptable salts.

7. Compound according to claim 1, characterized in that $R^1=R^2=H$, trans, Y=H, $R^3=C_6H_5—$, and its pharmaceutically acceptable salts.

8. Compound according to claim 1, characterized in that $R^1=R^2=H$, cis, Y=H, $R^3=CH_3—$, and its pharmaceutically acceptable salts.

9. Compound according to claim 1, characterized in that $R^1=R^2=H$, trans, Y=H, $R^3=CH_3—$, and its pharmaceutically acceptable salts.

10. Compound according to claim 1, characterized in that $R^1=R^2=CH_3—$, cis, Y=H, $R^3=4—H_2N—C_6H_4—$, and its pharmaceutically acceptable salts.

11. Compound according to claim 1, characterized in that $R^1=R^2=CH_3—$, trans, Y=H, $R^3=4—H_2N—C_6H_4—$, and its pharmaceutically acceptable salts.

12. Compound according to claim 1, characterized in that $R^1=R^2=CH_3—$, cis, Y=H, $R^3=4—CH_3CONH—C_6H_4—$, and its pharmaceutically acceptable salts.

13. Compound according to claim 1, characterized in that $R^1=R^2=CH_3—$, trans, Y=H, $R^3=4—CH_3CONH—C_6H_4—$, and its pharmaceutically acceptable salts.

14. Process for the preparation of novel compounds of the general formula I and their pharmaceutically acceptable salts according to claim 1, characterized in that compounds of general formula II

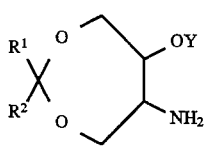

II wherein $R^1$, $R^2$ and Y have the meanings described in claim 1, are reacted with reactive derivatives of sulfonic acids of general formula III $R^3SO_2—Z$   III wherein $R^3$ has the meanings described in claim 1, and Z represents a halogen atom with atomic number 9 to 17 or $—OSO_2R^3$ group, wherein $R^3$ has the meanings described in claim 1, in water-miscible or water-unmiscible inert organic solvents, in the presence or absence of water, in the presence or absence of inorganic or organic acid-binding agents, at a temperature from $-50°$ C. to $+50°$ C., and, optionally, the obtained compounds are converted with inorganic bases or metal alcoholates into pharmaceutically acceptable salts.

15. Process for the preparation of novel compounds of the general formula I and their pharmaceutically acceptable salts according to claim 1, characterized in that compounds of general formula IV

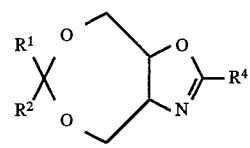

IV wherein $R^1$, $R^2$ and $R^4$ have the meanings as described in claim 1, are reacted with reactive derivatives of sulfonic acids of general formula III, $R^3SO_2—Z$   III wherein $R^3$ and Z have the meanings as described in claim 14, in non-aqueous inert organic solvents, in the presence of inorganic or organic acid-binding agents and, optionally, the obtained derivatives of the general formula I (Y=—$COR^4$) are hydrolyzed or alcoholyzed into derivatives of formula I (Y=H) and, if desired, the obtained compounds are converted with inorganic bases or metal alcoholates into pharmaceutically acceptable salts.

16. Process for the preparation of novel compounds of general formula I and of their pharmaceutically acceptable salts according to claim 1, characterized in that compounds of general formula V

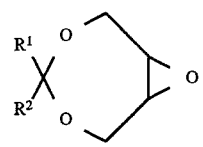

V wherein $R^1$ and $R^2$ have the meanings described in claim 1, are reacted with sulfonamides of general formula VI $R^3SO_2NH_2$   VI wherein $R^3$ has the meanings described in claim 1, in the absence or presence of inert organic solvents, at temperatures from $25°$ C. to $300°$ C. and, optionally, the obtained compounds are convened with inorganic bases or metal alcoholates into pharmaceutically acceptable salts.

17. Process for the preparation of novel compounds of the general formula I and of their pharmaceutically acceptable salts according to claim 1, characterized in that compounds of general formula VII

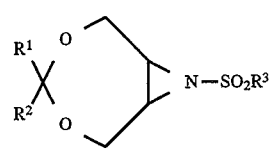

VII wherein $R^1$, $R^2$ and $R^3$ have the meanings described in claim 1, are hydrolyzed in water or in water-miscible organic solvents, in the presence of inorganic bases, at temperatures from $0°$ C. to $150°$ C. and, optionally, the obtained compounds are converted with inorganic bases or metal alcoholates into pharmaceutically acceptable salts.

18. Pharmaceutical preparations for the therapy of diabetes mellitus, characterized in that they comprise a sulfonamide of the general formula I according to claim 1 as the active component.

19. Pharmaceutical preparations for the treatment of hypoglycemia, comprising:

an effective amount of compounds according to claim 1 or their physiological salts.

20. Pharmaceutical preparations for the treatment of hypoglycemia, comprising:

an effective amount of compounds according to claim 2 or their physiological salts.

* * * * *